(12) United States Patent
Simpson et al.

(10) Patent No.: US 7,811,293 B2
(45) Date of Patent: Oct. 12, 2010

(54) SYSTEM AND METHOD FOR RAPID PLACEMENT OF CHEST TUBES

(75) Inventors: Philip J. Simpson, 3185 Pioneer Pl., Escondido, CA (US) 92025-7662; David G. Matsuura, 859 Summersong Ct., Encinitas, CA (US) 92024; Walter Dean Gillespie, 1327 Pacific Beach Dr., #11, San Diego, CA (US) 92109; Chris K. Salvino, 401 E. Ontario, Apt. 4406, Chicago, IL (US) 60611; Jim Trinchera, Leucadia, CA (US)

(73) Assignees: Philip J. Simpson, Escondido, CA (US); Walter Dean Gillespie, San Diego, CA (US); David G. Matsuura, Encinitos, CA (US); Chris K. Salvino, Scottsdale, AZ (US)

( * ) Notice: Subject to any disclaimer, the term of this patent is extended or adjusted under 35 U.S.C. 154(b) by 984 days.

(21) Appl. No.: 10/770,829

(22) Filed: Feb. 2, 2004

(65) Prior Publication Data

US 2005/0273116 A1 Dec. 8, 2005

Related U.S. Application Data

(60) Provisional application No. 60/444,326, filed on Jan. 31, 2003, provisional application No. 60/444,345, filed on Jan. 31, 2003.

(51) Int. Cl.
*A61F 11/00* (2006.01)
*A61M 5/32* (2006.01)

(52) U.S. Cl. ........................ 606/108; 604/174

(58) Field of Classification Search ............... 606/108; 604/21, 19, 48, 93.01, 164.01, 167.01, 167.06, 604/166.01, 95.04, 174
See application file for complete search history.

(56) References Cited

U.S. PATENT DOCUMENTS 3,237,624 A * 3/1966 Jinkens et. al. ............... 604/324

(Continued)

FOREIGN PATENT DOCUMENTS

CN 2207149 9/1995

(Continued)

OTHER PUBLICATIONS

European Search Report issued Mar. 17, 2010 in corresponding EP 04707425.

*Primary Examiner*—Kevin C Sirmons
*Assistant Examiner*—Michael J Anderson
(74) *Attorney, Agent, or Firm*—David H. Jaffer; Pillsbury Winthrop Shaw Pittman LLP

(57) ABSTRACT

A method and system are disclosed for rapid placement of tubes within a body cavity that includes placing a compliant cannula over a probe tip of a cutting device until the probe tip extends beyond the cannula, incising the tissue covering body cavity to create an opening therein, inserting the probe tip of the cutting device until the cannula placed thereon extends into the incision, removing the probe tip while leaving the cannula inserted within the incision, introducing a distal end or tip of a tube into the cannula a predetermined distance, and removing the cannula over the tube while retaining the tube in position within the body cavity. The device includes a sealing portion which attaches to the body without sutures and having an opening therethrough, and a tube which passes through the opening of the seal and mates thereto without sutures.

13 Claims, 20 Drawing Sheets

U.S. PATENT DOCUMENTS

| | | | |
|---|---|---|---|
| 4,221,215 A * | 9/1980 | Mandelbaum | 604/327 |
| 4,439,189 A * | 3/1984 | Sargeant et al. | 604/317 |
| 4,716,901 A * | 1/1988 | Jackson et al. | 606/185 |
| 4,778,446 A * | 10/1988 | Jensen | 604/27 |
| 5,045,052 A * | 9/1991 | Sans | 600/32 |
| 5,098,392 A | 3/1992 | Fleischhacker et al. | |
| 5,221,263 A | 6/1993 | Sinko et al. | |
| 5,232,453 A * | 8/1993 | Plass et al. | 604/180 |
| 5,389,080 A * | 2/1995 | Yoon | 604/167.03 |
| 5,429,598 A | 7/1995 | Waxman et al. | |
| 5,478,333 A | 12/1995 | Asherman | |
| 5,545,179 A | 8/1996 | Williamson | |
| 5,545,517 A | 8/1996 | Thompson et al. | |
| 5,685,859 A * | 11/1997 | Kornerup | 604/180 |
| 5,797,882 A | 8/1998 | Purdy et al. | |
| 5,807,341 A | 9/1998 | Heim | |
| 5,897,531 A * | 4/1999 | Amirana | 604/180 |
| 5,919,203 A | 7/1999 | Husted et al. | |
| 6,045,535 A * | 4/2000 | Ben Nun | 604/167.01 |
| 6,056,730 A * | 5/2000 | Greter | 604/319 |
| 6,056,766 A * | 5/2000 | Thompson et al. | 606/185 |
| 6,074,380 A * | 6/2000 | Byrne et al. | 606/1 |
| 6,110,154 A * | 8/2000 | Shimomura et al. | 604/256 |
| 6,579,281 B2 * | 6/2003 | Palmer et al. | 606/1 |
| 6,811,546 B1 * | 11/2004 | Callas et al. | 604/167.06 |
| 7,244,245 B2 * | 7/2007 | Purow et al. | 604/180 |
| 7,276,075 B1 * | 10/2007 | Callas et al. | 606/191 |
| 7,377,898 B2 * | 5/2008 | Ewers et al. | 600/208 |
| 2002/0042607 A1 * | 4/2002 | Palmer et al. | 606/1 |
| 2002/0133168 A1 * | 9/2002 | Smedley et al. | 606/108 |
| 2002/0161377 A1 * | 10/2002 | Rabkin | 606/108 |
| 2003/0088245 A1 * | 5/2003 | Woloszko et al. | 606/41 |
| 2003/0233073 A1 * | 12/2003 | Purow et al. | 604/174 |
| 2005/0273116 A1 * | 12/2005 | Simpson et al. | 606/108 |

FOREIGN PATENT DOCUMENTS

| | | |
|---|---|---|
| EP | 0488332 | 10/1998 |
| WO | WO 03/008020 | 1/2003 |

* cited by examiner

A) FIG. 18A
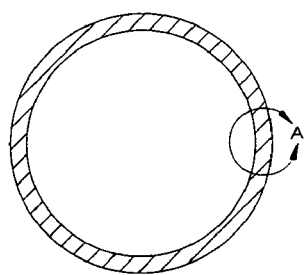
B)
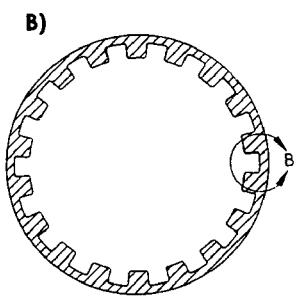
FIG. 18B
FIG. 18D
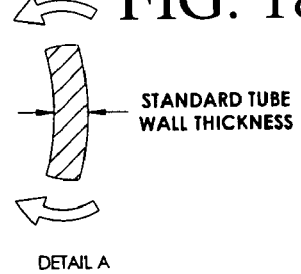
DETAIL A
FIG. 18E
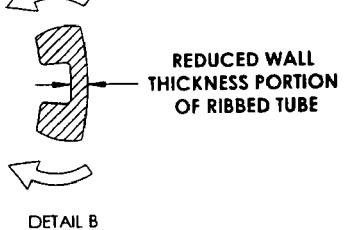
DETAIL B
FIG. 18C
C) 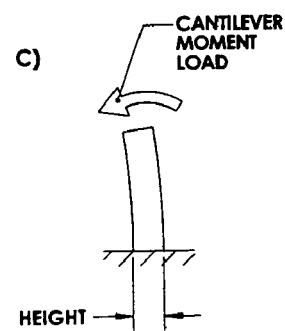

SYSTEM AND METHOD FOR RAPID PLACEMENT OF CHEST TUBES

RELATED APPLICATION

This application claims priority from provisional U.S. patent application Ser. No. 60/444,345, filed Jan. 31, 2003 and having the same inventors and same title as the present application, and which is incorporated herein by reference.

This application also claims priority from U.S. patent application Ser. No. 60/444,326, file Jan. 31, 2003 entitled Tissue Manipulation and Incision System and Method, having partly common inventors, (herein referred to as the "Related Application") and filed on even date herewith filed herewith and incorporated herein by reference.

FIELD OF THE INVENTION

The present invention relates to methods and apparatus for performing a rapid tube thoracostomy, and more particularly relates to methods and apparatus for performing a rapid tube thoracostomy using conformable tubes and cannula.

BACKGROUND OF THE INVENTION

A trocar generally comprises an obturator and a cannula. The obturator has a pyramid-shaped piercing tip at one end, and moves the piercing tip into tissue to form a hole to provide access to a body cavity or a target tissue. The cannula is located around the obturator. The cannula is inserted into the body cavity together with the obturator through the hole formed by the piercing tip. Such a trocar, therefore, forms a pathway in the inside of the cannula for inserting an endoscope or a surgical tool into the body cavity, by extracting or withdrawing the obturator from the cannula, which is inserted into the body cavity. Known methods of sealing the tissue to the cannula include the use of sutures and/or adhesive tape in order to maintain the position of the cannula and provide a fluid and air tight seal. However, this method fails to provide adequate barrier or an appropriate seal for fluid and/or gases. Therefore what is needed is a system and method for providing an air and fluid tight seal without the use of sutures and/or adhesive tape.

SUMMARY OF THE INVENTION

The present invention provides methods and systems for safely and easily performing a rapid tube thoracostomy. Tube thoracostomy is a method for allowing the sterile drainage of fluid or air from the pleural space utilizing a semi-rigid drainage tube. In at least some implementations, the present invention also minimizes the need for exposed sharp instruments such as scalpels.

More particularly, the present invention provides a chest tube installation system which includes, in an exemplary embodiment, a chest tube insertion device, a diametrically compliant cannula, a chest tube and a chest tube pneumo seal/wound dressing. The chest tube insertion device utilizes a cutter such as that disclosed in the Related Application, referenced above, and incorporated herein by reference.

BRIEF DESCRIPTION OF THE FIGURES

FIGS. 18A-18E illustrate various details of some examples of chest tubes in accordance with the present invention.

DETAILED DESCRIPTION OF THE INVENTION

Figure 1:
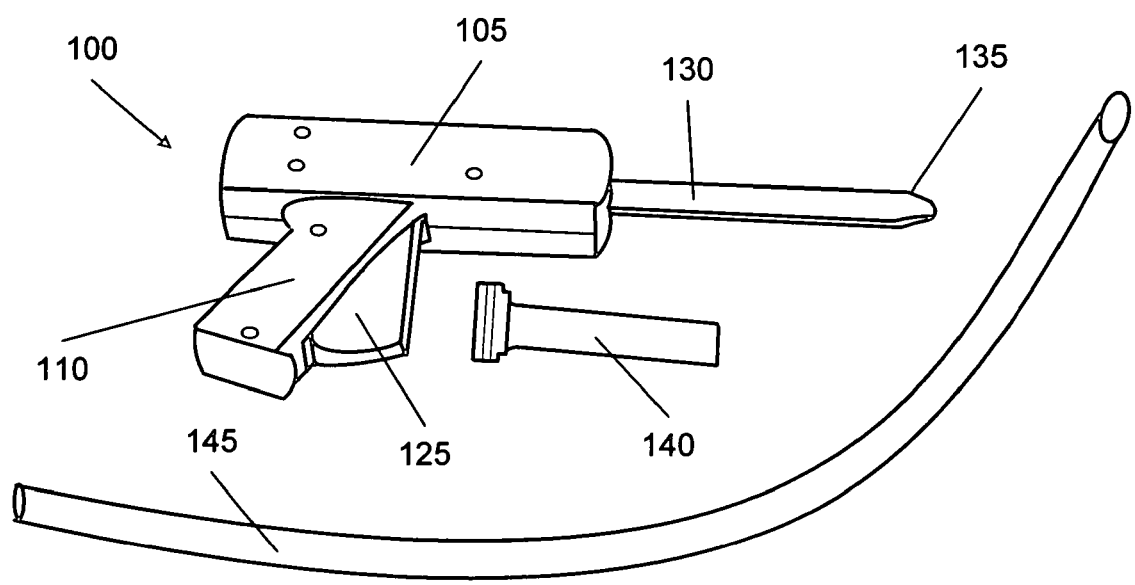
FIG. 1 illustrates in perspective view generally an insertion gun, a cannula and chest tube in accordance with one aspect of the present invention.
Figure 2:
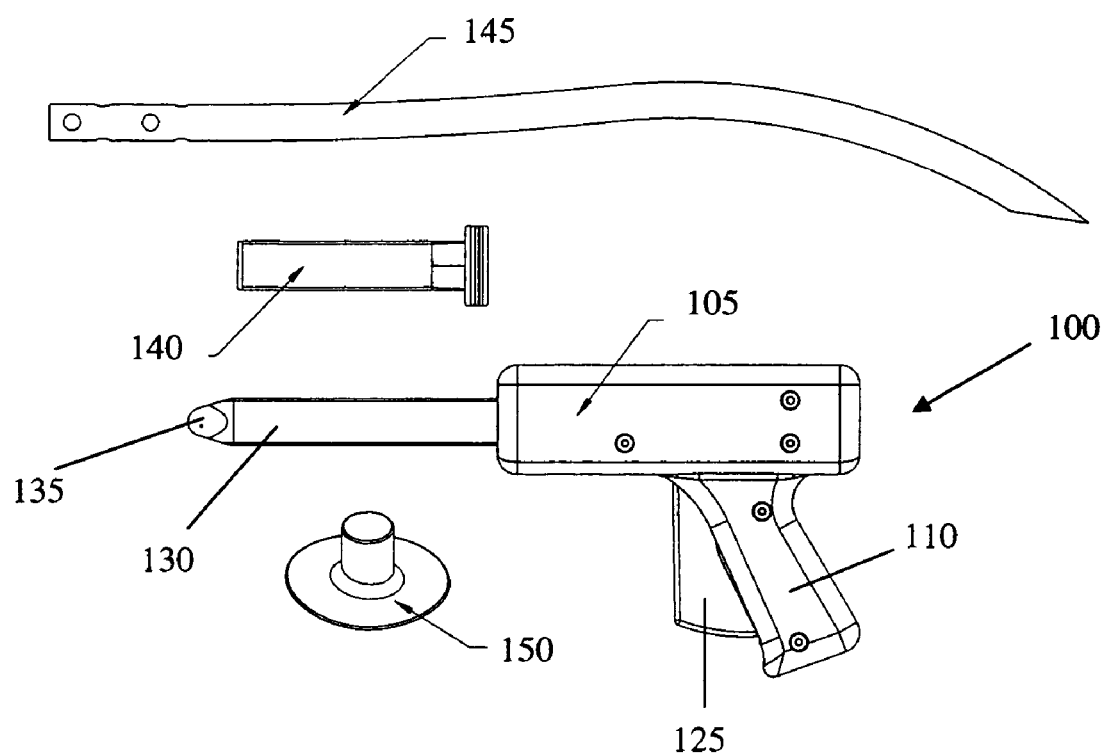
FIG. 2 illustrates, in side elevation view, in addition to the system of FIG. 1, a seal in accordance with one aspect of the present invention.

Referring first to FIGS. 1 and 2, a system for chest tube insertion in accordance with the present invention is shown generally. A chest tube insertion device 100, which may also be thought of as a cutting and insertion gun, includes a housing 105, a handle 110 with a trigger 125, a probe tip 130 having a cutting tip 135 at the distal end thereof, a cannula 140, a chest tube 145 and a seal 150. The cutting tip 135 may be of the type described in the Related Application.

Referring next to FIGS. 3-10, the process for inserting a chest tube according to the present invention can be better appreciated. The chest tube insertion procedure using this system is safer, faster, and easier than other known methods. Although not a required part of the present invention, clinicians considering insertion of a chest tube typically include the steps of selecting a site, preparing the patient and then draping the area, followed by anesthetizing the site. The anesthesia can be of any acceptable type; one typical approach is 5 to 15 ml of 1% lidocaine delivered through a syringe and small gauge needle.

Figure 3:
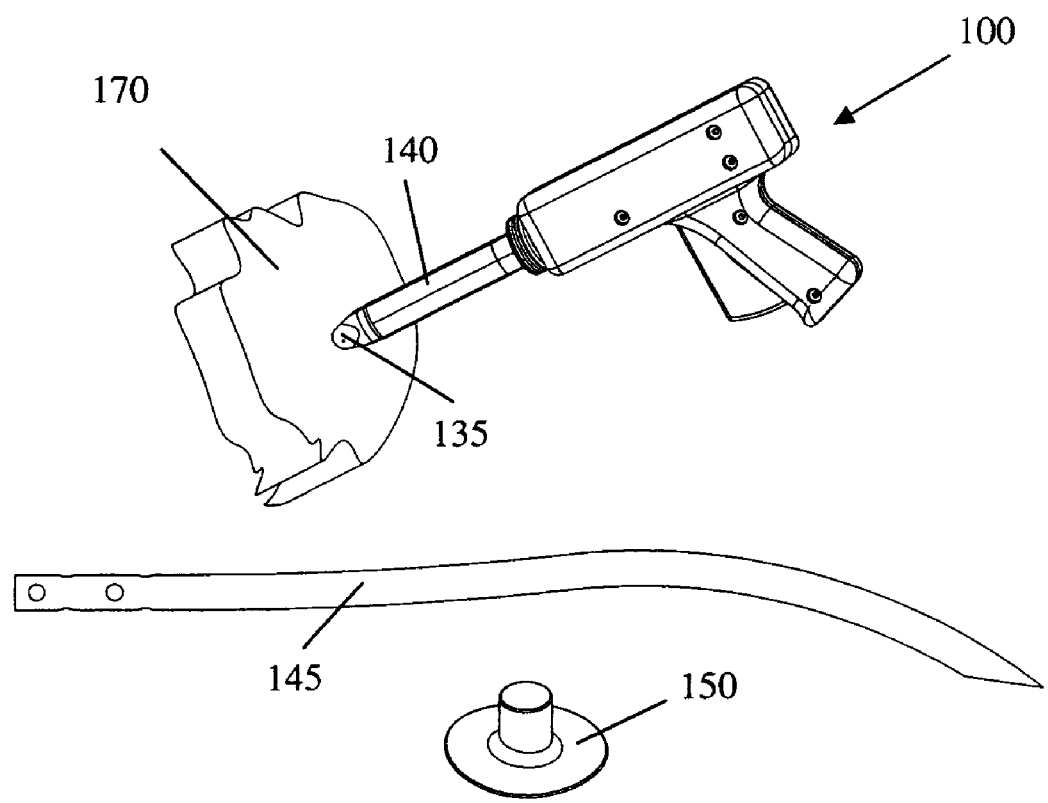
FIG. 3 illustrates the gun of FIG. 1 applied to an area of tissue characteristic of a patient needing aid, with the cannula on the probe of the gun.
Figure 4:
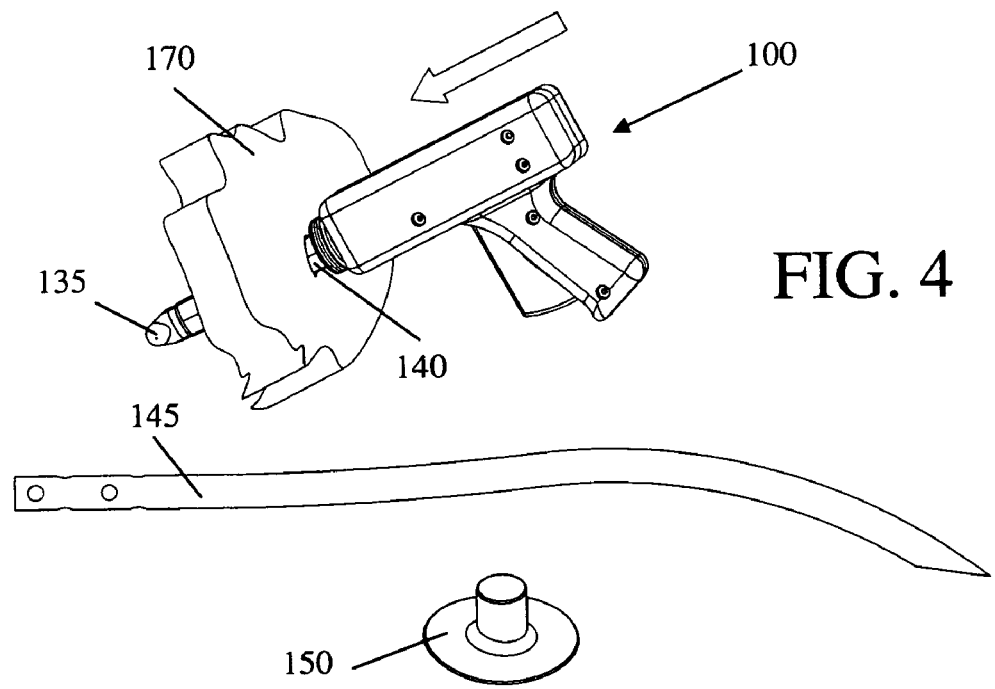
FIG. 4 illustrates the gun of FIG. 1 inserted partly into the patient after appropriate cuts have been made.
Figure 5:
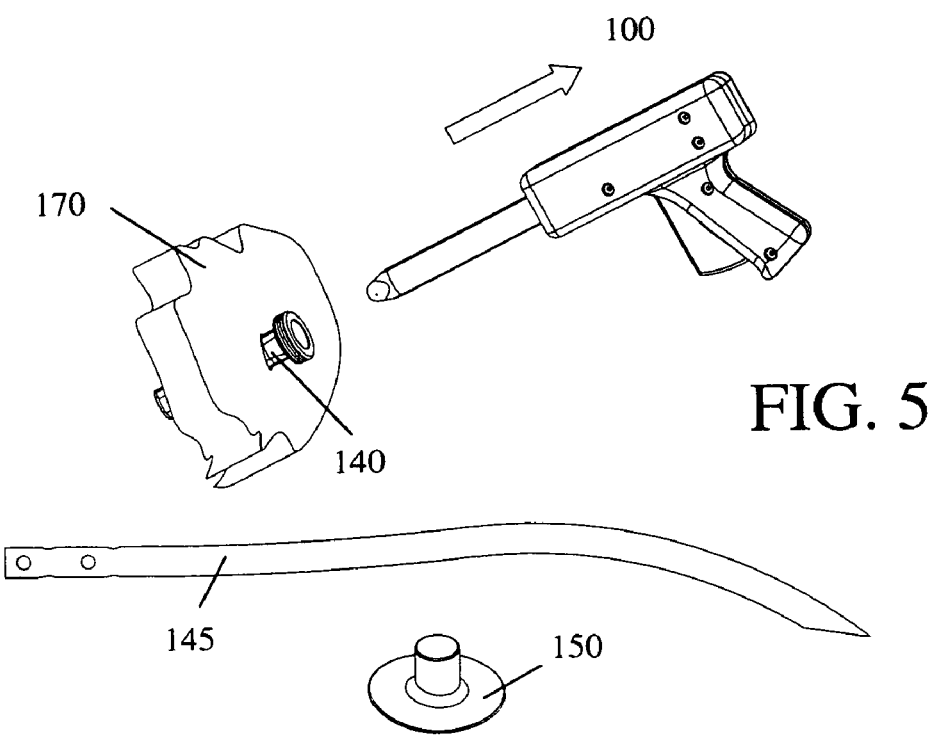
FIG. 5 illustrates the gun removed from the patient with the cannula remaining inserted into the patient.
Figure 6:
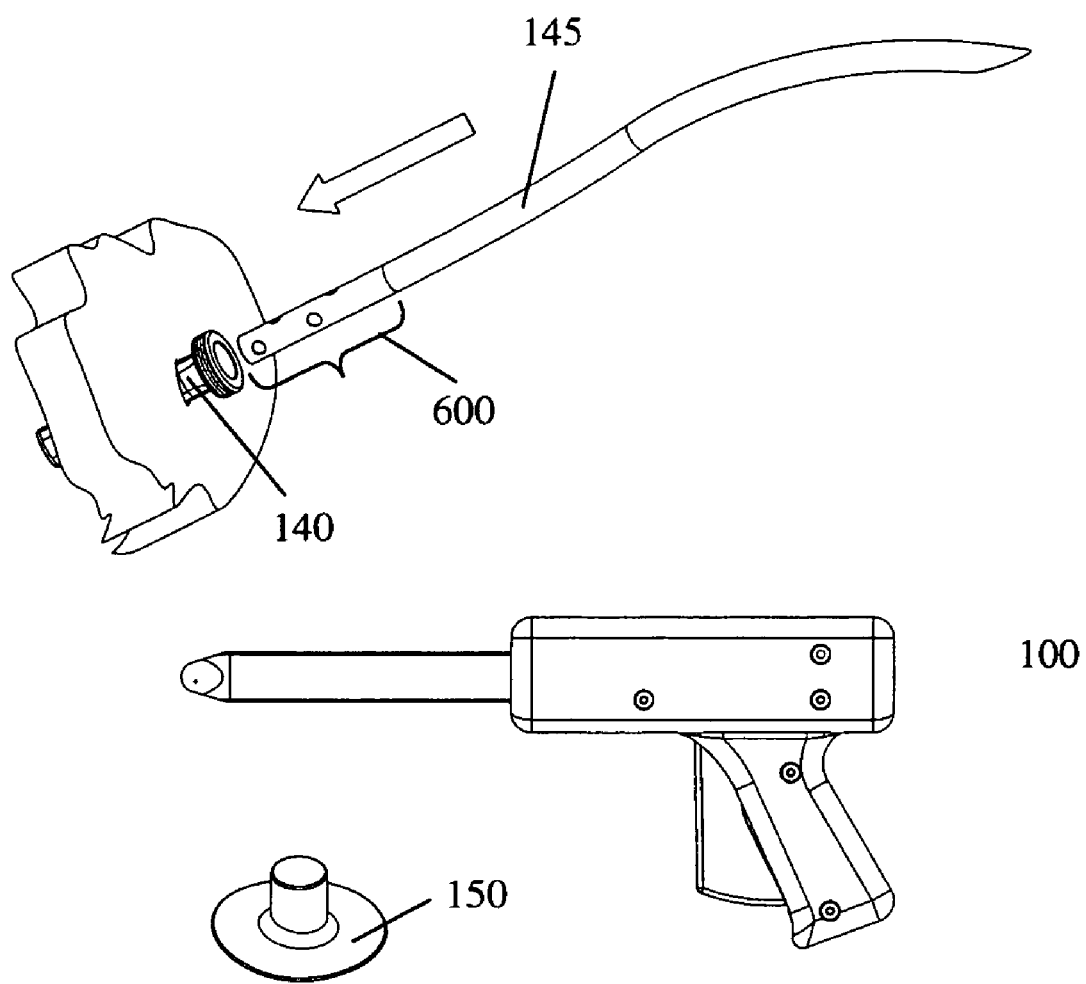
FIG. 6 illustrates the insertion of the chest tube through the cannula of FIG. 5.
Figure 7:
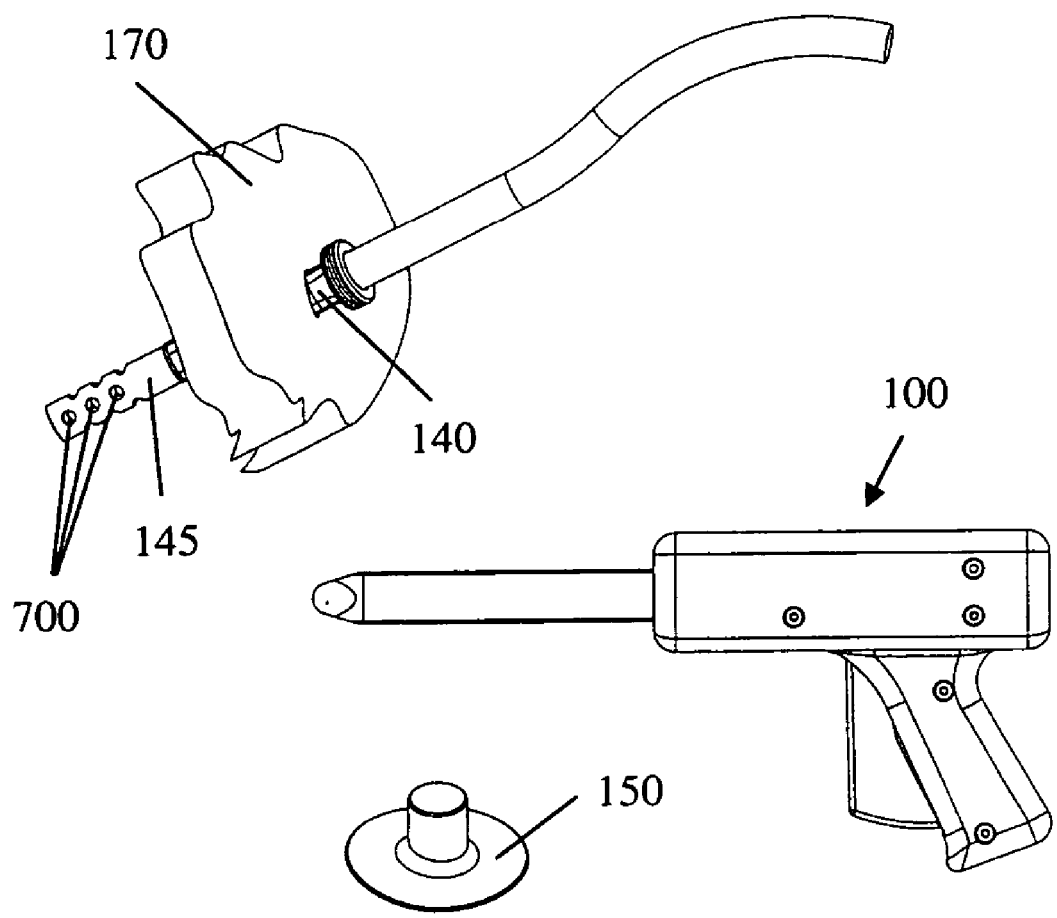
FIG. 7 illustrates the chest tube inserted into the patient through the cannula.
Figure 8:
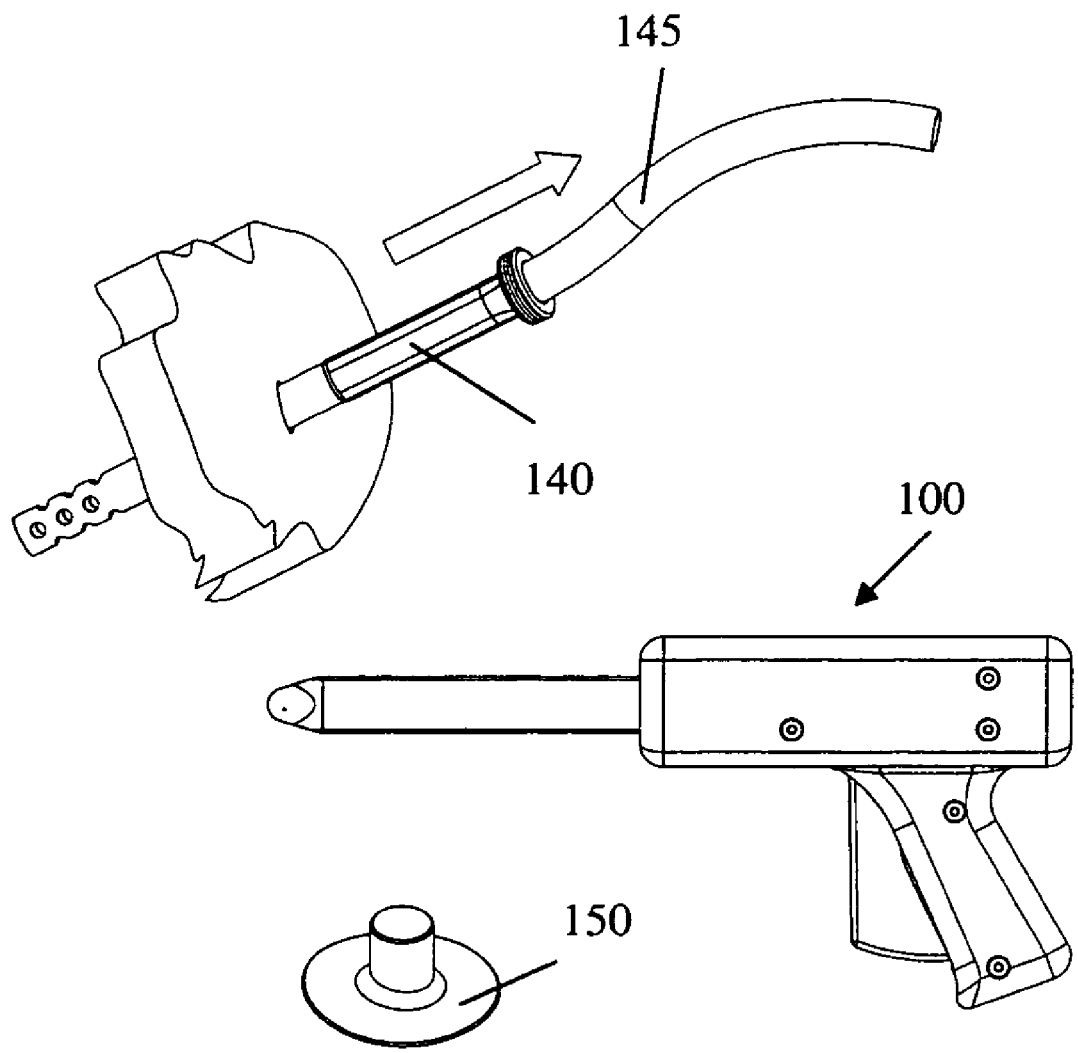
FIG. 8 illustrates the removal of the compliant cannula over the chest tube.
Figure 9:
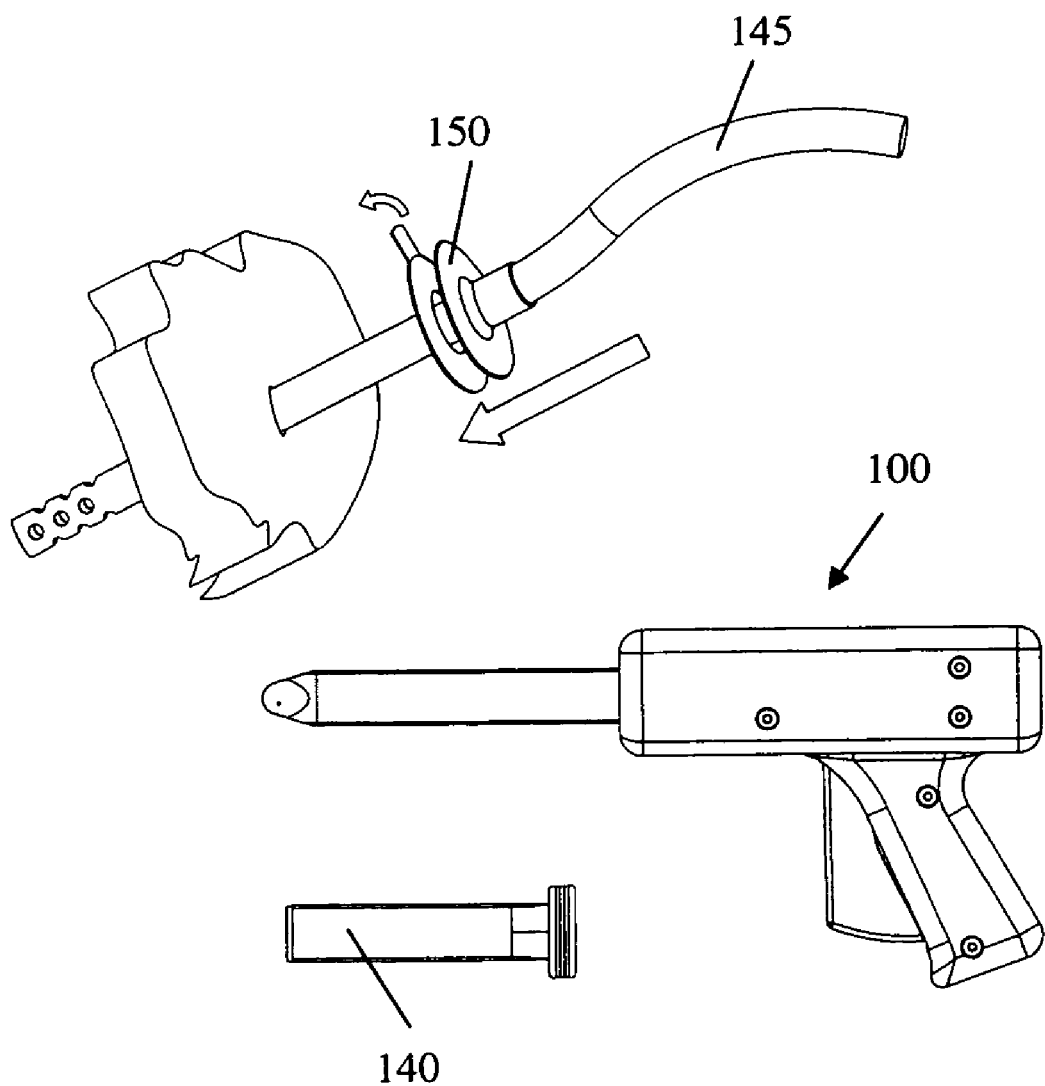
FIG. 9 illustrates the application of a sealing element over the chest tube.
Figure 10:
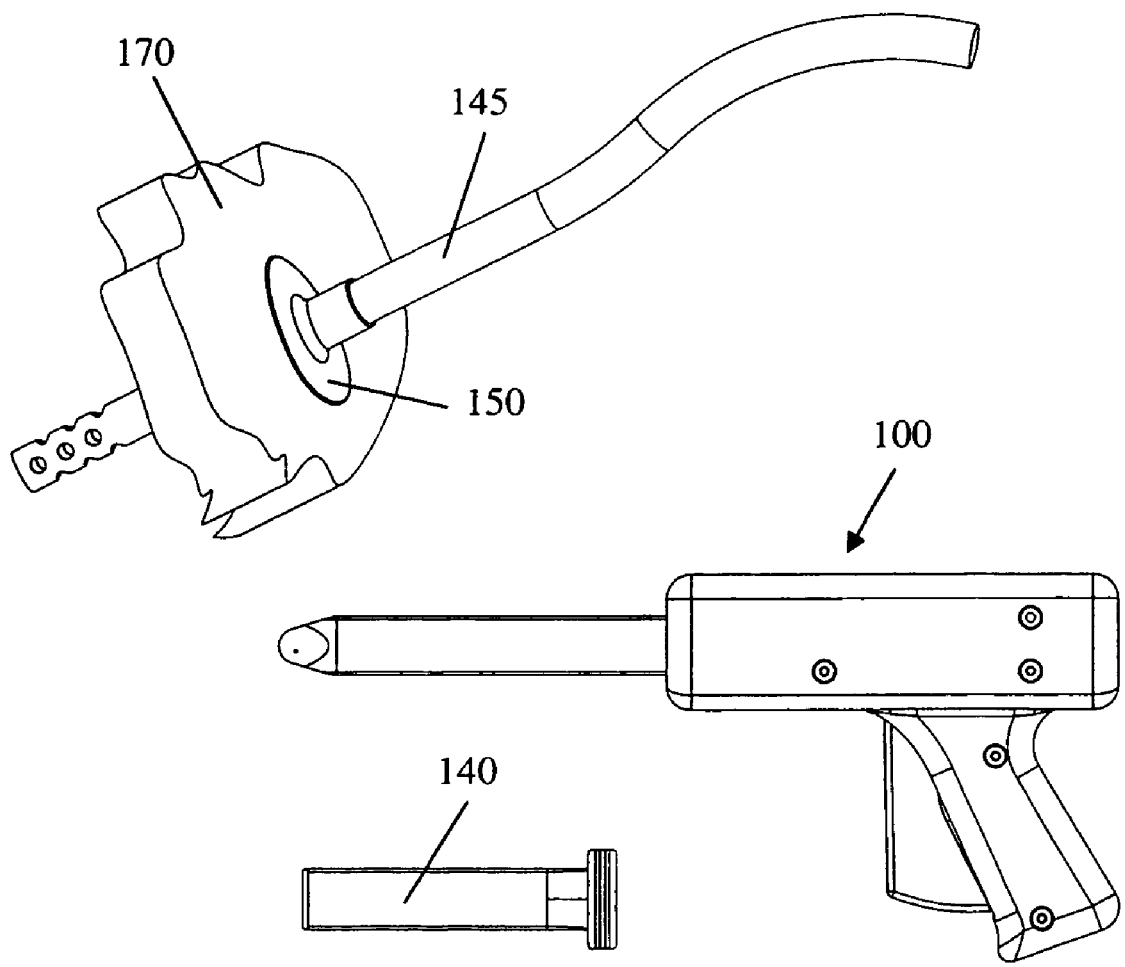
FIG. 10 illustrates the sealing of the wound with the seal over the chest tube, thus completing the chest tube installation.

Following the foregoing preliminary steps, the chest tube insertion procedure in accordance with the present invention proceeds as follows:

1. Make an incision through skin to the pleural space with the chest tube insertion device, or gun, 100. Start by placing a cannula 140 over the probe tip or shaft 130 of the device 100 until the cutting tip 135 extends beyond the cannula 140.
2. Place the device 100 against the patient's target tissue 170 as shown in FIG. 3. Visually aligning the shaft 130 of the device in the desired direction. Firmly press the distal tip 135 into the skin and actuate the trigger 125. Actuation of the trigger will initiate a cutting event, creating an incision 175, as shown in FIG. 4. Each cutting event will cut approximately 1 mm in depth as long as the cutting tip is maintained appropriately against the tissue 170. As the device 100 cuts through skin, the device 100 may be used as a blunt dissection device, and may be thought of as a blunt tip obturator.
3. Once the tip of the probe 130 extends into the pleural cavity in the desired amount, the cannula will also extend into the cavity as shown in FIG. 4. Withdrawal of the gun 100 from the incision 175 can be achieved while leaving the cannula 140 in place within the patient as shown in FIG. 5.
4. As shown best in FIG. 6, introduce the distal tip 600 of the chest tube 145 into the cannula 140.
5. Advance the tube 145 until all of the transverse drain holes 700 of the chest tube 145 are within the pleural space, as shown in FIG. 7.
6. Withdraw the cannula 140 over the chest tube 145 while holding the chest tube 145 in place, best shown in FIG. 8.

Then, as is typical of thoracostomies, the clinician will typically take the additional steps of suturing the skin on both sides of the chest tube and tying the tube in place with the tag ends of the suture; applying sterile petroleum gel over the incision to create an airtight seal and cutting notches in sterile gauze to fit around the chest tube, followed by securing the gauze and tube in place using a suitable surgical tape.

The present invention provides an improvement over the standard methods of securing the chest tube in place. The chest tube insertion procedure in accordance with the present invention continues as follows:

7. Place the sealing structure 150 over the chest tube 145 and slide the sealing structure down the chest tube towards the tissue 170. Remove a protective cover from an adhesive lower surface of the sealing structure 150 and attach the sealing structure 150 to the tissue 170. The lower surface of the sealing structure 150 is conformed to and adhered to the tissue 170. See FIGS. 9 and 10.

From the foregoing, a method of rapidly placing a chest tube according to the invention can be appreciated. However, the chest tube insertion device 100 may be implemented in any of a variety of designs, just as the cutting tip 135 may be implemented in a variety of ways as discussed in the Related Application. Several of these implementations are described in connection with FIGS. 11A through 15.

Figure 11:
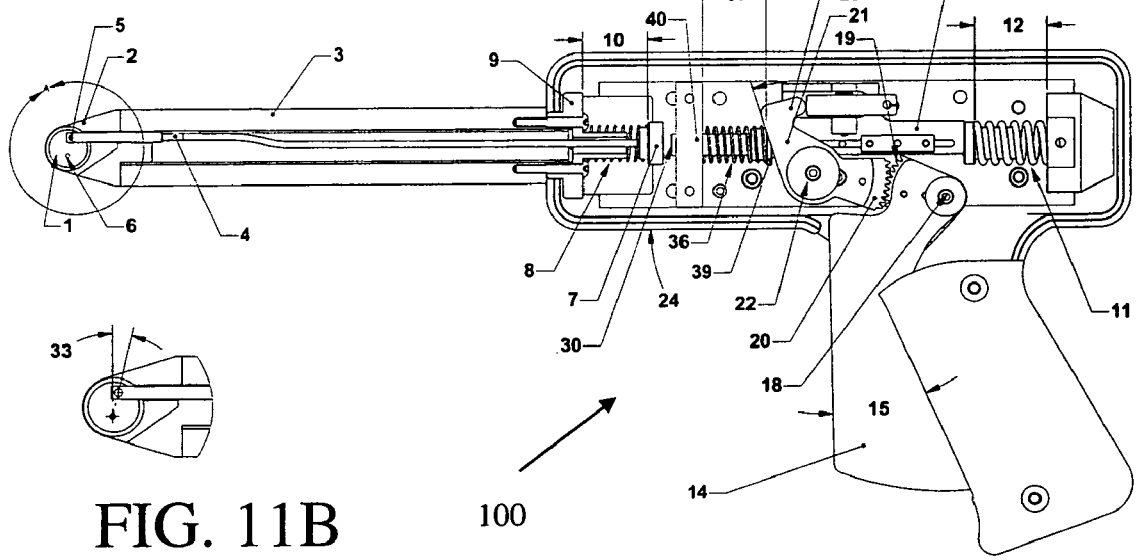
FIGS. 11A-11B show in cut-away view one implementation of the gun of FIG. 1, with FIG. 11B providing a detail view of the cutting tip of the gun.
Figure 12:
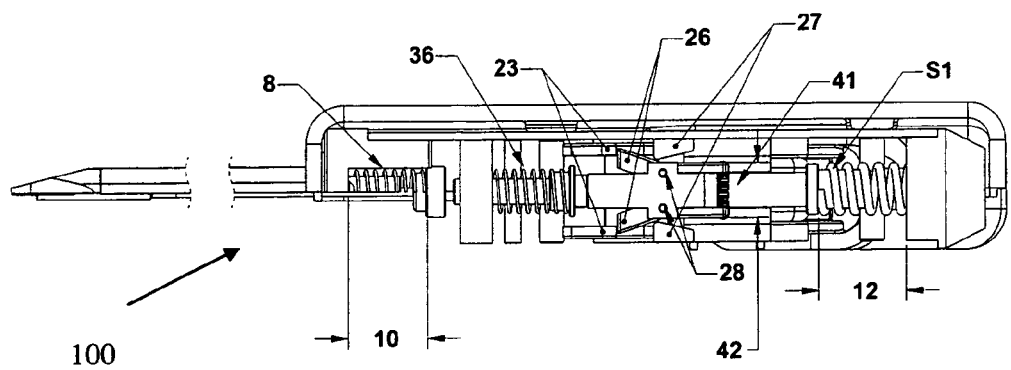
FIG. 12 shows in cut-away view certain details of the implementation of FIG. 11A.

Referring next to FIGS. 11A-11B and 12, a first implementation of the chest tube insertion device shown generally at 100 may be better appreciated. An eccentrically mounted circular blade 1 is housed inside a bearing block 2 and is attached to the bearing block 2 by an axle 6. The blade 1 need not be an eccentrically mounted circular blade, but may instead be any of the forms shown in the Related Application. The bearing block 2 is located at the distal end of a shaft or probe 3, which is similar to the probe 130 of FIG. 1. The blade 1 is also connected to the distal end of an input rod 4 by a pivot pin 5. A compression spring 8, is constrained at a compressed height 10, by a flange 7 at the proximal end of the input rod 4 and a wall 9 inside the mechanism housing. The force from the compression spring 8, translates through the input rod 4 to the eccentrically mounted blade 1 through the pivot pin 5. The force acting on the pivot pin 5 results in a moment about the axle 6 which keeps the blade 1 recessed inside the bearing block 2 until the operator initiates a cutting event.

Figure 13:
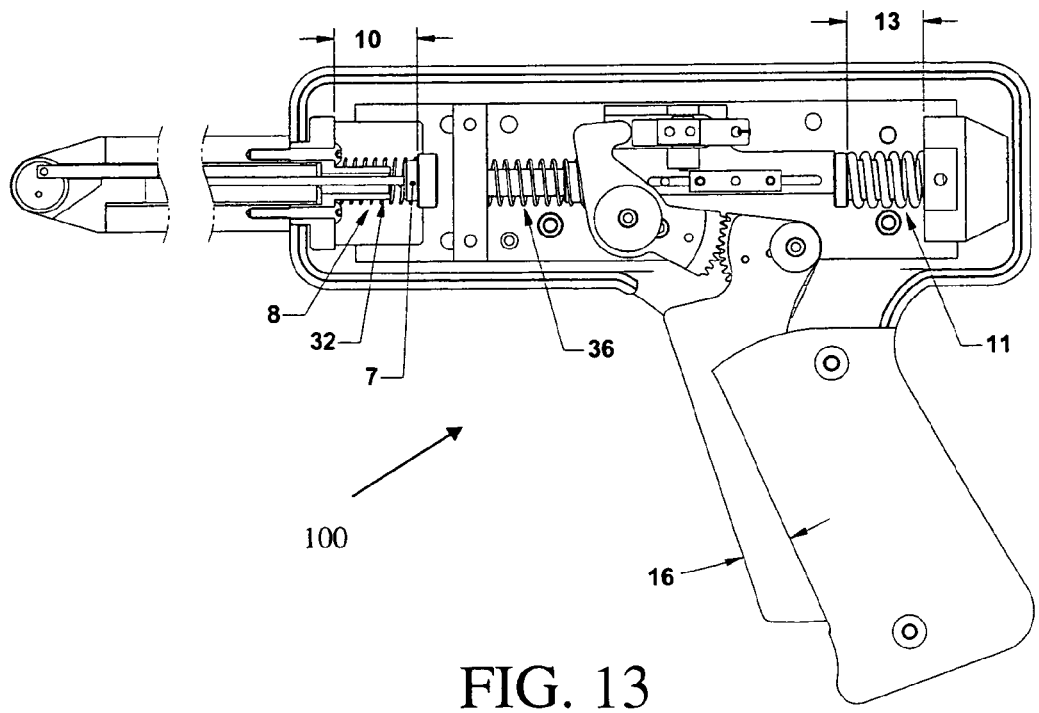
FIG. 13 illustrates in cut-away view the gun of FIG. 11A with the trigger at approximately mid-point.
Figure 14:
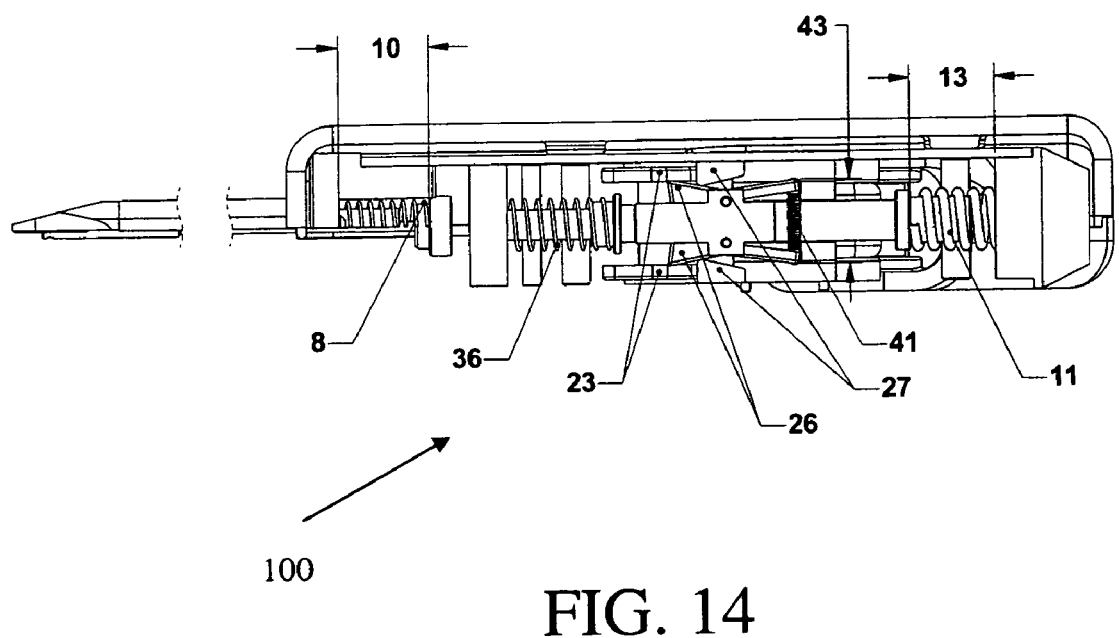
FIG. 14 illustrates in more detail an implementation of the gun of FIG. 13.
Figures 15A, 15B:
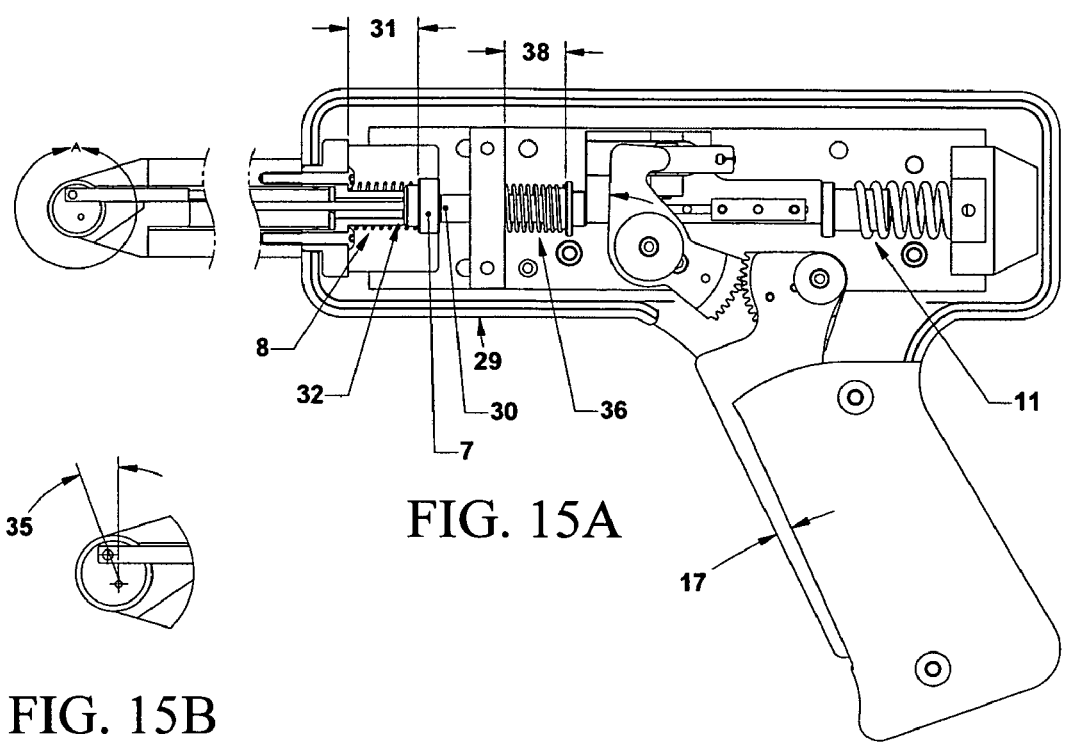
FIG. 15A illustrates the implementation of the gun of FIG. 11A with the trigger fully retracted.
FIG. 15B illustrates in detail cut-away view the cutting tip of FIG. 15A.
Figure 16A:
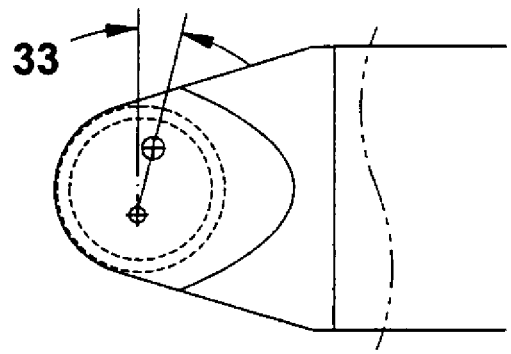
FIGS. 16A-16D illustrate the eccentric nature of the cutting tip of the gun.
Figure 16B:
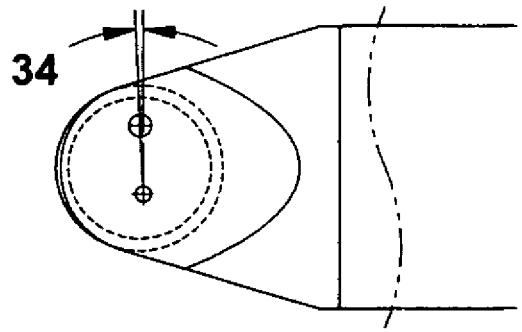
Figure 16C:
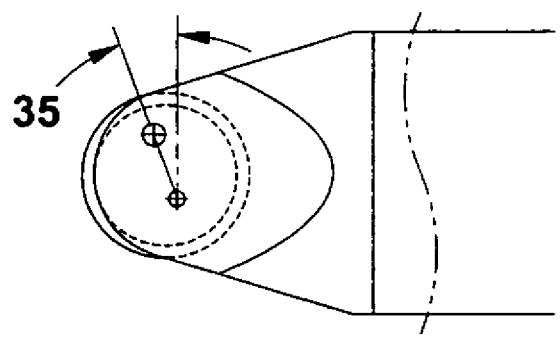
Figure 16D:
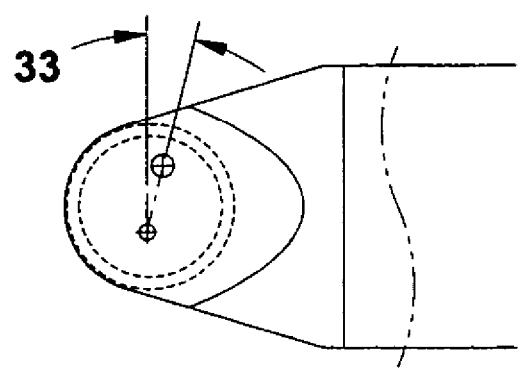
Figures 17A, 17B, 17C, 17D:
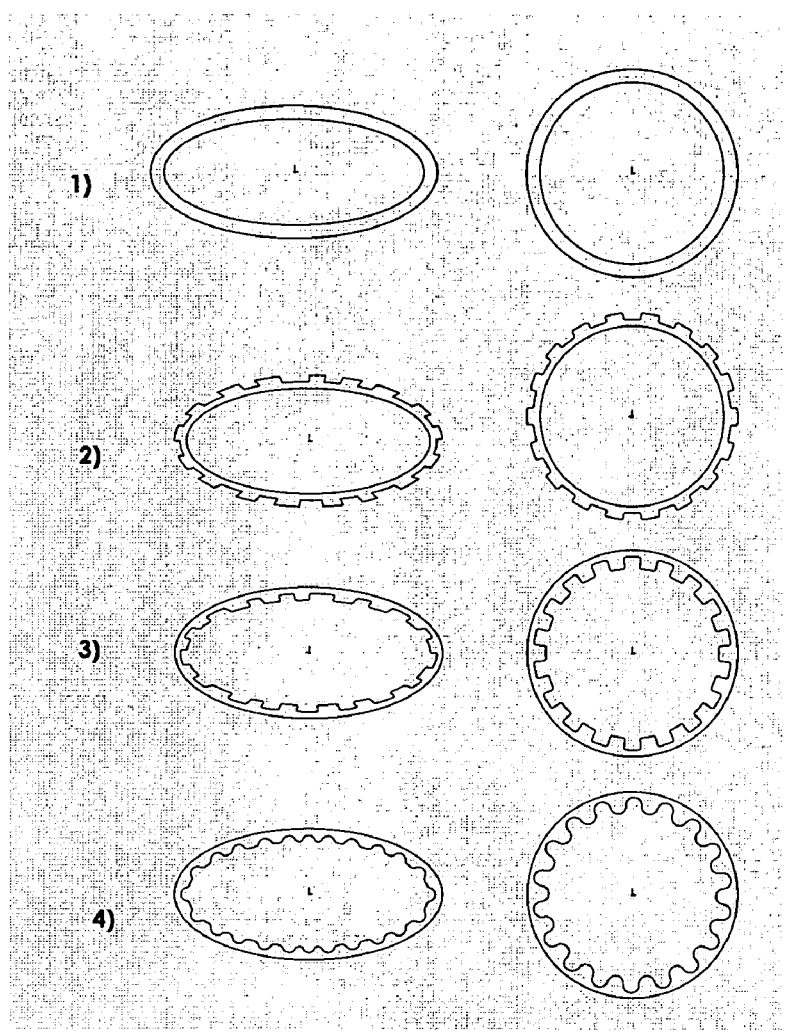
FIGS. 17A-17D illustrate cross-sectional view of various chest tubes, both in compressed and uncompressed views.

To initiate a cutting event, the operator moves an input lever or trigger 14, which is similar to the trigger 125 of FIG. 1, from a stationary position 15, as shown in FIGS. 11A-11B and the more detailed view of FIG. 12, through an intermediate position 16 as shown in FIG. 13 to a final position 17 shown in FIG. 15. As the input lever 14 is moved, it pivots about a lever axle 18. The angular rotation of the lever 14 is translated through one segment of circular gear teeth 19 mounted concentric to the lever axle 18, to a meshing segment of circular gear teeth 20 attached to a cam 21. The cam 21 is allowed to rotate about a shaft 22 as it is motivated to do so by motion of the gear teeth 20.

The cam 21 profile is exaggerated through a pair of elongated members 23 which contact a momentum storage mass 25 through a matching pair of latches 26 which are attached to the mass 25 by pins 28. The latches 26 are able to rotate about the pins 28 that connect them to the mass 25. The mass 25 is constrained to move only longitudinally on an axis co-linear with the shaft 3. Angular cam motion is translated to distal-to-proximal linear motion of the mass 25 as the cam 21 rotates from a stationary position 24 shown in FIG. 11A to a final position 29 as shown in FIG. 15. In the particular implementation shown, the mass 25 is moved rearward or toward the proximal end of the device 100.

Distal-to-proximal linear motion of the mass 25 causes the angled outer surfaces of the matching pair of latches 26 to encounter stationary protrusions 27. As detailed in FIG. 14, the protrusions 27 act on the angled outer surfaces of the latches 26 so that the latches 26 rotate about their pivot pins 28 until they no longer contact the cam members 23. Simultaneously, the mass 25 compresses a spring 11 from its free length 12 as depicted in FIG. 11, as it travels proximally, to a compressed length 13 as depicted in FIG. 13. Release of the latches 26 from the cam members, enable the resultant force created by compression of the spring 11 to act on the momentum storage mass 25 thereby accelerating it in a proximal to distal direction. Potential energy stored in the spring 11 at the compressed length 13 is converted to kinetic energy as the mass 25 is accelerated.

The proximal to distal motion of the mass 25 causes its distal most face 30 to strike the proximal end of the rod 4. The mass 25 and the rod 4 continue with a proximal to distal motion until the flange 7 strikes a travel limiting structure 32. The proximal to distal motion of the rod 4 acts on the blade 1 such that it rotates about the axle 6, which attaches the blade 1 to the bearing block 2. As the mass 25 and the rod 4 travel proximal to distally, the blade 1 rotates about the axle 6, which connects the blade 1 to the bearing block 2. Depicted in FIGS. 16A-D, as the blade 1 rotates, it emerges from the bearing block 2 from a stationary position to a fully exposed position when the rod 4 encounters the travel limiting structure 32.

As the momentum storage mass 25 travels in a proximal to distal direction it compresses a spring 36 constrained between a flange 39 and stationary internal structure 40. Force stored in the spring 36 created by compressing the spring 36 to a pre-loaded height 38 acts on the mass 25 once its proximal to distal motion has been halted by the travel limiting structure 32. The force generated by the spring 36 causes the mass 25 to move in a distal to proximal direction until equilibrium is achieved. With the mass 25 reset, the compression spring 8 that is in contact with the proximal end of the rod 4 acts on the rod 4 to move the rod 4 in a distal to proximal direction thereby recessing the blade 1 to a safe position inside the bearing block 2.

The operator resets the mechanism after initiating a cutting event by releasing the input lever 14. The input lever 14 then returns to the stationary position 15 by means of a spring (not shown) in contact with the input lever 14, causing the input lever 14 to rotate about the lever axle 18. Motion of the lever 14 causes the cam 21 to move to its stationary position 24. As the elongated members 23 move to their stationary positions the latches 26 attached to the mass 25 are acted on by an extension spring 41 to return the latches 26 to their position 42. The mechanism is now reset and ready for another operator initiated cutting event.

Optionally, an additional user control may be incorporated into the device 100 to hold the cutting element fully extended when actuated. This alternative control allows the clinician to optionally use the device as a sharp trocar as well.

One aspect of the chest tube insertion device is that the shaft 130 is, in an least some embodiments, substantially ovate in cross section. This allows for passage of a larger bore transversely compliant cannula to be inserted between the ribs without dilating the rib cage. At room temperature, standard chest tubes are fairly diametrically compliant, across the transverse axis of the tube, and become much more compliant at body temperature. Therefore, standard chest tubes can be passed through a substantially ovate cannula. Thus, a larger chest tube can be inserted with significantly less pain to the patient. Optionally, the cannula may be pre-formed with an ovate cross section of a less compliant material.

Another aspect of the device is the use of preferentially compliant chest tubes. Standard chest tubes are formed with uniform wall thickness. These tubes are formed with walls heavy enough to prevent kinking across the transverse axis of the tube due to longitudinal bending loads. When using a substantially ovate cannula, the load required to pass the circular chest tube through the cannula, can be substantially reduced through the use of a tube that is preferentially more diametrically compliant, across the transverse axis, than standard tubes.

In some embodiments of the invention, it is desirable to use a generally thinner walled tube, which may for example be formed by extrusion, with walls formed with a multiplicity of longitudinal ribs, scallops or splines as shown in FIGS. 17A-17D. The ribs may be on the inside or outside of the tube, and may take any of a wide variety of shapes. The space between the ribs form flexure zones, thus allowing the tube to be more diametrically compliant than a standard tube. Another purpose of the ribs is to provide adequate section modulus to prevent transverse kinking of the tube when bent under normal loading conditions, such as shown by the equations set forth below and shown in FIGS. 18A-18E. Furthermore, design of interior ribs could provide patent lumens, to prevent complete shut off, even when exposed to extreme loading conditions. Additionally the ribs add sufficient section to provide adequate resistance to tensile loads.

Cantilever moment load $$Modulus_{section} := \frac{Base \cdot Height^3}{12}$$

$$Moment := 2 \cdot \frac{deflection \cdot Modulus_{Elastic} \cdot Modulus_{section}}{Length^2}$$

Figures 19A, 19B:
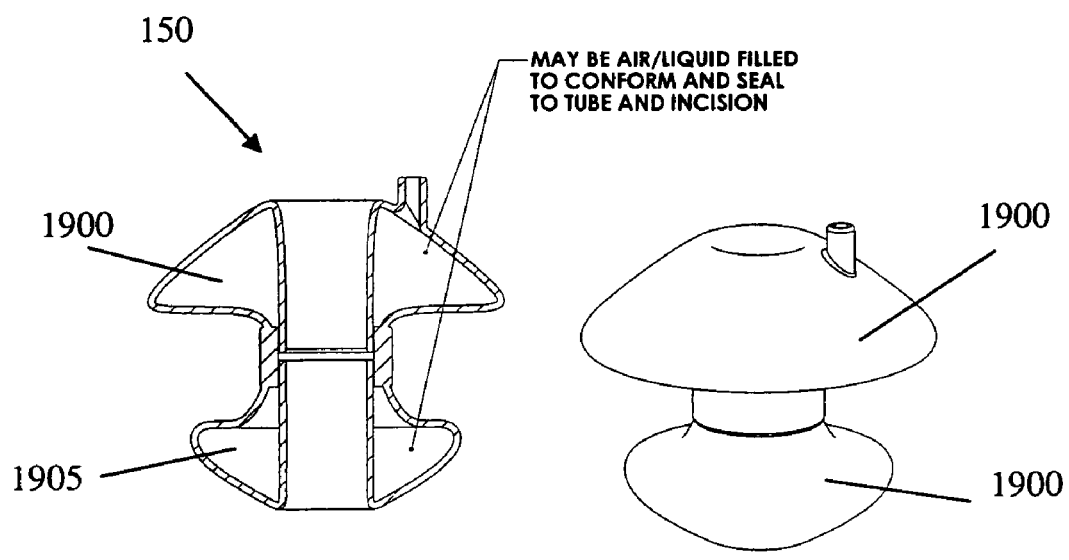
FIGS. 19A-19B illustrate perspective and cross-sectional side views of a seal in accordance with the invention.
Figure 20:
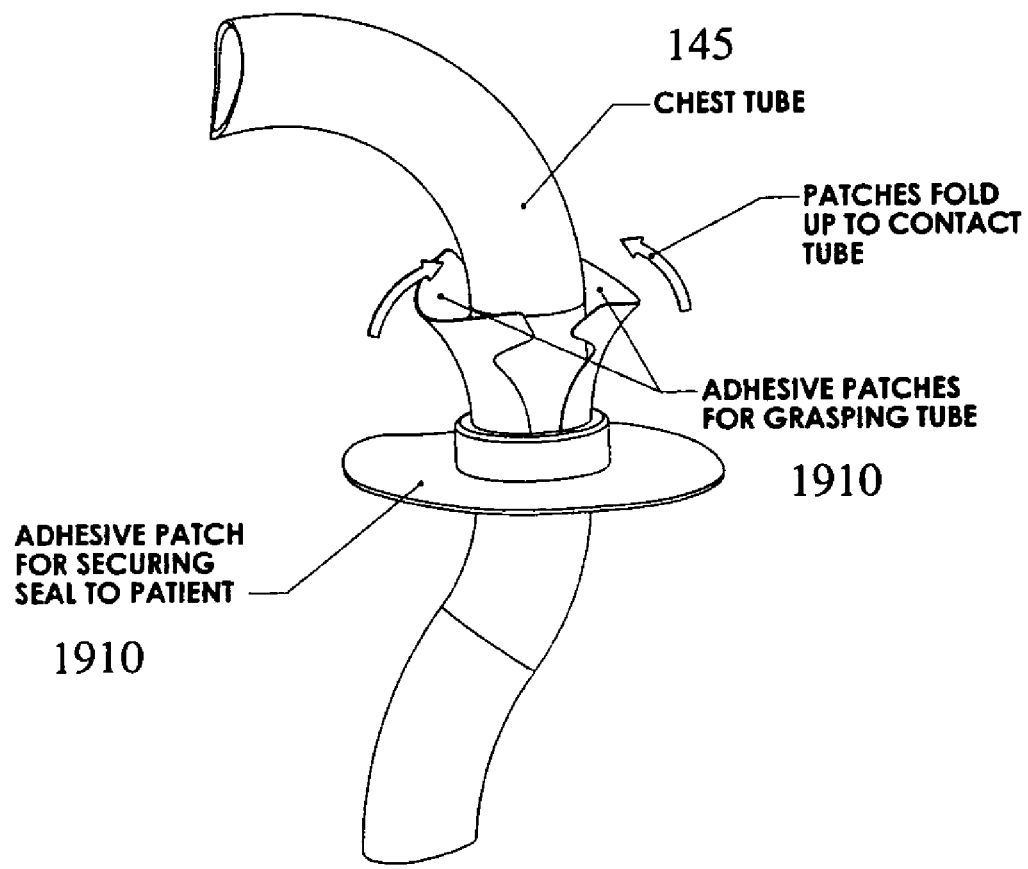
FIG. 20 illustrates an adhesive method for attachment of the chest tube assembly to a patient.
Figures 21A, 21B, 21C:
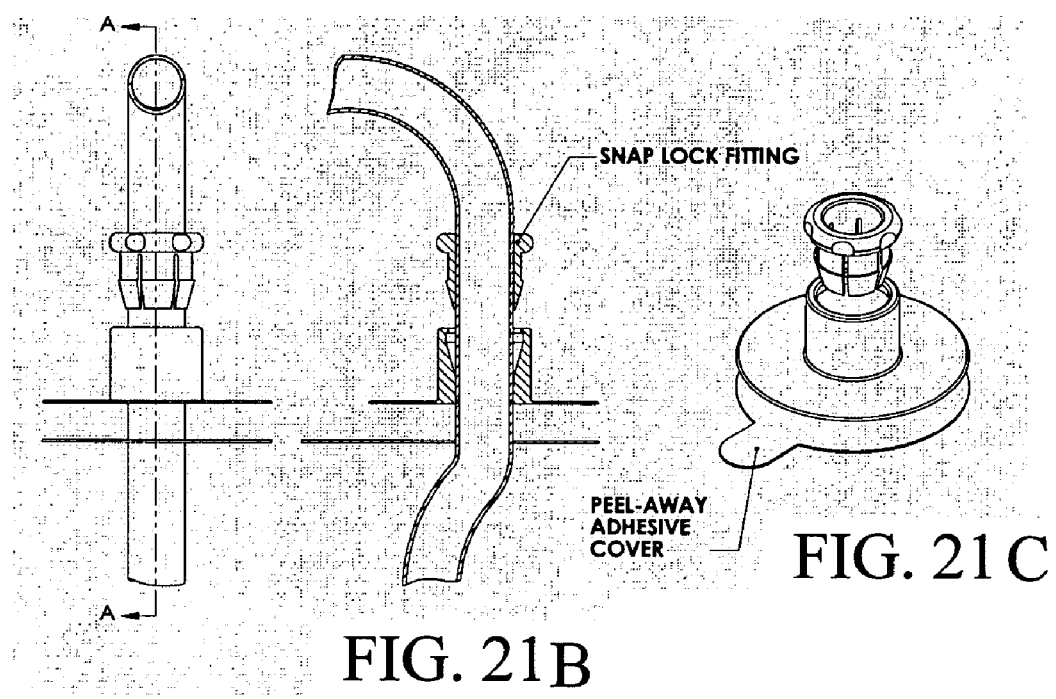
FIGS. 21A-21C illustrate, respectively, a side elevation view of a snap lock fitting for attachment of the chest tube to a patient, a cross-sectional side view, and a perspective view of the snap lock fitting itself.

Another innovative aspect of the some embodiments of the system of the invention is the use of an elastomeric pneumo-seal, such as shown at 150 in FIG. 2 and better seen in FIGS. 19A-19B. The term pneumo-seal is used herein to refer to a seal that acts as a barrier to prevents the flow of fluids and gases. The pneumo-seal 150 can be formed of a compliant material with upper flange 1900 and lower flange 1905, and may have pressure sensitive adhesive attachment areas 1910 as shown in FIGS. 20 and 21 to adhere to and seal to the patient and the chest tube. The pressure sensitive seal or barrier formed by the pneumo-seal is accomplished without stitches or sutures. The pneumo-seal may be pre-loaded and reside on the cannula 140 or may be used as a separate device.

The sealing structure 150 is shown in FIG. 20 as having a generally disk-shaped lower portion, the bottom surface of which is covered by adhesive for attaching the sealing structure 150 to the patient. See also FIG. 10. The adhesive bottom surface of the sealing structure 150 is protected by a cover which can be readily peeled away when ready to be attached to the patient. See FIGS. 9 and 21C. Referring again to FIG. 20, the generally disk-shaped lower portion of the sealing structure 150 includes a central aperture through which the chest tube 145 passes. The sealing structure further includes two adhesive patches 1910 for attaching the sealing structure 150 to the chest tube 145, the adhesive patches 1910 being attached to the lower portion along diametrically opposed parts of the circumference of the central aperture. The adhesive patches 1910 are configured to fold up along the length of the chest tube 145 from the plane of the generally disk-shaped lower portion, each adhesive patch wrapping widthwise only partially around the circumference of the chest tube.

Figure 22A:
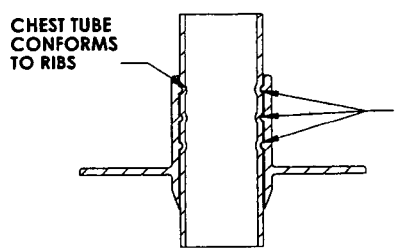
FIGS. 22A-22B illustrate in cross-sectional side view the attachment of the snap lock fitting of FIGS. 21A-21C to a patient.
Figure 22B:
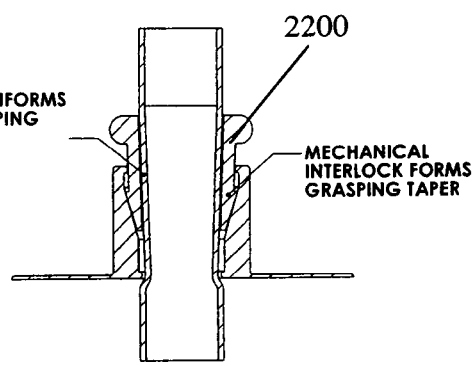

Alternatively, the pneumo-seal device 150 may have a fitting 2200 that mates to a matching fitting integrally formed with the chest tube or, as shown in FIG. 22B, provided as a snap-lock fitting added to the chest tube. The purpose of the fitting is to mechanically attach the tube to the patient patch and to form an air-tight seal.

Alternatively, mechanical sealing ribs (FIG. 22A) may also replace the adhesive contacting tube. The basic configuration of the pneumo-seal 150 can also be used for other cannulations into the body such as central venous lines and other drainage tubes. Optionally, the device may be molded from a transparent material, such as Pebax, to allow visualization of the wound through the device. The advantages of the pneumo-seal device include that it is faster than faster than cutting bandages, requires no use of scissors, is faster than suturing or tying, requires no needles, does not require petroleum gel to form seal (thus allowing use of standard wound dressing tapes.

Alternatively, mechanical sealing ribs (FIG. 22A) may also replace the adhesive contacting tube. In FIG. 22A the sealing structure 150 is shown to have a cylindrical upper portion with a plurality of circumferential ribs on the inner surface of the cylindrical upper portion. The chest tube 145 is shown to be sufficiently compliant to conform to the ribbed inner surface of the sealing structure 150. The plurality of annular ribs are spaced along the length of the generally cylindrical upper portion.

The basic configuration of the pneumo-seal 150 can also be used for other cannulations into the body such as central venous lines and other drainage tubes. Optionally, the device may be molded from a transparent material, such as Pebax, to allow visualization of the wound through the device. The advantages of the pneumo-seal device include that it is faster than cutting bandages, requires no use of scissors, is faster than suturing or tying, requires no needles, does not require petroleum gel to form a seal (thus allowing use of standard wound dressing tapes).

It will thus be appreciated that a new and novel method of chest tube insertion has been disclosed, as well as a new and novel chest tube insertion system and components thereof. Among the advantages offered by one or more of implementations of the invention are a controlled depth of cut, According to some embodiments of the present invention, a rapid tube insertion system for inserting tubes into a pleural space in a chest comprises: a cutting device having a probe tip which extends distally; a compliant cannula capable of being placed over the probe tip, the end of the probe tip extending beyond the cannula, the cannula being capable of being inserted into an incision into the pleural space; a chest tube having a distal end adapted to be inserted through the compliant cannula and a proximal portion extending outwardly therefrom, and the cannula being capable of being passed over the proximal portion of the tube; and a sealing structure which mates to the tube and is adapted to create a pneumo-seal substantially at the junction of the sealing structure and the exterior surface of the chest, wherein the sealing structure does not substantially penetrate the chest wall and the sealing structure attaches to the exterior surface of the chest and the tube without sutures.

a retractable blade offering increasing user and patient safety, greater safety for the clinician. Having fully disclosed a variety of implementations of the present invention, it will be appreciated by those skilled in the art that numerous alternatives and equivalents exist which do not materially alter the invention described herein. Therefore, the invention is not intended to be limited by the foregoing description, but instead only by the appended claims.

We claim:

1. A rapid tube insertion system for inserting tubes into a pleural space in a chest comprising
    a cutting device having a probe tip which extends distally,
    a compliant cannula capable of being placed over the probe tip, the end of the probe tip extending beyond the cannula, the cannula being capable of being inserted into an incision into the pleural space,
    a chest tube having a distal end adapted to be inserted through the compliant cannula and a proximal portion extending outwardly therefrom, and the cannula being capable of being passed over the proximal portion of the tube, and
    a sealing structure which mates to the tube and is adapted to create a pneumo-seal substantially at the junction of the sealing structure and the exterior surface of the chest, wherein the sealing structure does not substantially penetrate the chest wall and the sealing structure attaches to the exterior surface of the chest and the tube without sutures,
    wherein the sealing structure includes a generally cylindrical upper portion with a plurality of annular ribs on the inner surface of the cylindrical upper portion and wherein the chest tube is sufficiently compliant to conform to the ribs.

2. The rapid tube insertion system of claim 1 wherein the tube is a drain tube.

3. The rapid tube insertion system of claim 1 wherein the compliant cannula has an ovate shape.

4. The rapid tube insertion system of claim 1 wherein the compliant cannula has a portion thereof formed of a less compliant material than the remainder thereof.

5. The rapid tube insertion system of claim 1 wherein the tube includes longitudinal reinforcement to prevent kinking.

6. The rapid tube insertion system of claim 1 wherein the sealing structure includes a generally disk-shaped lower portion having a central aperture through which the chest tube passes.

7. The rapid tube insertion system of claim 1 wherein the lower portion of the sealing structure includes an adhesive-coated lower surface, for attaching to the exterior surface of the chest.

8. The rapid tube insertion system of claim 1 wherein the lower portion of the sealing structure includes a removable protective cover, for protecting the adhesive-coated lower surface until it is ready to be attached to the exterior surface of the chest.

9. The rapid tube insertion system of claim 1 wherein the sealing structure is capable of being passed over the proximal portion of the chest tube.

10. The rapid tube insertion system of claim 1 wherein the probe tip of the cutting device has an ovate cross-section.

11. The rapid insertion system of claim 1 wherein the compliant cannula has a preformed ovate cross-section.

12. The rapid tube insertion system of claim 1 wherein the plurality of annular ribs are spaced along the length of the generally cylindrical upper portion.

13. The rapid tube insertion system of claim 1 wherein the plurality of annular ribs are integral to the inner surface of the generally cylindrical upper portion forming a ribbed inner surface, and wherein the chest tube is sufficiently compliant to conform to the ribbed inner surface.

* * * * *